United States Patent
Bar-Even et al.

(10) Patent No.: US 10,053,712 B2
(45) Date of Patent: Aug. 21, 2018

(54) USE OF ENZYMES WHICH CATALYZE PYRUVATE SYNTHESIS FROM FORMATE AND ACETYL-COA AND BACTERIA EXPRESSING SAME

(71) Applicant: Yeda Research and Development Co. Ltd., Rehovot (IL)

(72) Inventors: Arren Bar-Even, Tel-Aviv (IL); Ron Milo, Kfar-Saba (IL); Elad Noor, Rehovot (IL); Lior Zelcbuch, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 66 days.

(21) Appl. No.: 15/101,097

(22) PCT Filed: Dec. 10, 2014

(86) PCT No.: PCT/IL2014/051080
§ 371 (c)(1),
(2) Date: Jun. 2, 2016

(87) PCT Pub. No.: WO2015/087327
PCT Pub. Date: Jun. 18, 2015

(65) Prior Publication Data
US 2017/0081682 A1    Mar. 23, 2017

Related U.S. Application Data

(60) Provisional application No. 61/913,940, filed on Dec. 10, 2013.

(51) Int. Cl.
| | | |
|---|---|---|
| C12P 7/40 | (2006.01) |
| C12N 1/20 | (2006.01) |
| C12N 9/10 | (2006.01) |
| C12N 15/52 | (2006.01) |
| C12P 5/00 | (2006.01) |
| C12P 5/02 | (2006.01) |
| C12P 7/06 | (2006.01) |
| C12P 7/16 | (2006.01) |
| C12P 7/26 | (2006.01) |
| C12P 7/64 | (2006.01) |

(52) U.S. Cl.
CPC .......... *C12P 7/40* (2013.01); *C12N 1/20* (2013.01); *C12N 9/1029* (2013.01); *C12N 15/52* (2013.01); *C12P 5/007* (2013.01); *C12P 5/023* (2013.01); *C12P 5/026* (2013.01); *C12P 7/06* (2013.01); *C12P 7/16* (2013.01); *C12P 7/26* (2013.01); *C12P 7/649* (2013.01); *C12Y 203/01054* (2013.01); *Y02E 50/343* (2013.01)

(58) Field of Classification Search
CPC combination set(s) only.
See application file for complete search history.

(56) References Cited

U.S. PATENT DOCUMENTS 5,879,915 A    3/1999    Loubiere et al.

FOREIGN PATENT DOCUMENTS

| WO | WO 2012/138942 | 10/2012 |
| WO | WO 2013/076144 | 5/2013 |
| WO | WO 2014/020599 | 2/2014 |
| WO | WO 2015/087327 | 6/2015 |

OTHER PUBLICATIONS

Supplementary European Search Report and the European Search Opinion dated Apr. 26, 2017 From the European Patent Office Re. Application No. 14869116.5. (7 Pages).
Zelcbuch et al. "Pyruvate Formate-Lyase Enables Efficient Growth of *Escherichia coli* on Acetate and Formate", Biochemistry, XP055361330, 55(17): 2423-2426, Published Online Apr. 19, 2016.
International Preliminary Report on Patentability dated Jun. 23, 2016 From the International Bureau of WIPO Re. Application No. PCT/IL2014/051080.
International Search Report and the Written Opinion dated Feb. 8, 2015 From the International Searching Authority Re. Application No. PCT/IL2014/051080.
Bar-Even et al. "Design and Analysis of Metabolic Pathways Supporting Formatotmphic Growth for Electricity-Dependent Cultivation of Microbes", Biochimica et Biophysica Acta, 1827: 139-147, Available Online Dec. 30, 2012. Section 9, Fig.2.
Brush et al. "Inactivation of *Escherichia coli* Pyruvate Formate-Lyase by Hypophosphite: Evidence for a Rate-Limiting Phosphorus-Hydrogen Bond Cleavage", Biochemistry, 27(6): 2217-2222, Mar. 22, 1988. Abstract, Fig.3, p. 2220, Last Para-p. 2221, First Para.
Knappe et al. "Pyruvate Formate-Lyase of *Escherichia coli*: The Acetyl-Enzyme Intermediate", European Journal of Biochemistry, 50(1): 253-263, Dec. 31, 1974. Figs.2B-4B, Table 3.
Communication Pursuant to Article 94(3) EPC dated Nov. 30, 2017 From the European Patent Office Re. Application No. 14869116.5. (4 Pages).

*Primary Examiner* — Kagnew H Gebreyesus

(57) ABSTRACT

An isolated microorganism is disclosed being genetically modified to express pyruvate formate lyase (PFL) or 2-ketobutyrate formate lyase, wherein acetyl-CoA of the microorganism is converted to pyruvate in the presence of formate in a single step reaction, wherein the net flux of the reaction is in the direction of pyruvate synthesis.
Uses of the microorganism and products comprising same are also disclosed.

18 Claims, 5 Drawing Sheets
(5 of 5 Drawing Sheet(s) Filed in Color)

SEQUENCE LISTING

<160> NUMBER OF SEQ ID NOS: 2

<210> SEQ ID NO 1
<211> LENGTH: 760
<212> TYPE: PRT
<213> ORGANISM: Escherichia coli

<400> SEQUENCE: 1

```
Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
                20                  25                  30

Asn Tyr Thr Pro Tyr Glu Gly Asp Glu Ser Phe Leu Ala Gly Ala Thr
            35                  40                  45

Glu Ala Thr Thr Thr Leu Trp Asp Lys Val Met Glu Gly Val Lys Leu
        50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95
```

-continued

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
            115                 120                 125

Glu Leu Asp Pro Met Ile Lys Lys Ile Phe Thr Glu Tyr Arg Lys Thr
        130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
        290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
        450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala

```
            515                 520                 525
Gly Leu Ser Val Ala Ala Asp Ser Leu Ser Ala Ile Lys Tyr Ala Lys
        530                 535                 540
Val Lys Pro Ile Arg Asp Glu Asp Gly Leu Ala Ile Asp Phe Glu Ile
545                 550                 555                 560
Glu Gly Glu Tyr Pro Gln Phe Gly Asn Asn Asp Pro Arg Val Asp Asp
                565                 570                 575
Leu Ala Val Asp Leu Val Glu Arg Phe Met Lys Lys Ile Gln Lys Leu
            580                 585                 590
His Thr Tyr Arg Asp Ala Ile Pro Thr Gln Ser Val Leu Thr Ile Thr
                595                 600                 605
Ser Asn Val Val Tyr Gly Lys Lys Thr Gly Asn Thr Pro Asp Gly Arg
        610                 615                 620
Arg Ala Gly Ala Pro Phe Gly Pro Gly Ala Asn Pro Met His Gly Arg
625                 630                 635                 640
Asp Gln Lys Gly Ala Val Ala Ser Leu Thr Ser Val Ala Lys Leu Pro
                645                 650                 655
Phe Ala Tyr Ala Lys Asp Gly Ile Ser Tyr Thr Phe Ser Ile Val Pro
            660                 665                 670
Asn Ala Leu Gly Lys Asp Asp Glu Val Arg Lys Thr Asn Leu Ala Gly
                675                 680                 685
Leu Met Asp Gly Tyr Phe His His Glu Ala Ser Ile Glu Gly Gly Gln
        690                 695                 700
His Leu Asn Val Asn Val Met Asn Arg Glu Met Leu Leu Asp Ala Met
705                 710                 715                 720
Glu Asn Pro Glu Lys Tyr Pro Gln Leu Thr Ile Arg Val Ser Gly Tyr
                725                 730                 735
Ala Val Arg Phe Asn Ser Leu Thr Lys Glu Gln Gln Gln Asp Val Ile
                740                 745                 750
Thr Arg Thr Phe Thr Gln Ser Met
        755                 760

<210> SEQ ID NO 2
<211> LENGTH: 246
<212> TYPE: PRT
<213> ORGANISM: Escherichia coli

<400> SEQUENCE: 2

Met Ser Val Ile Gly Arg Ile His Ser Phe Glu Ser Cys Gly Thr Val
1               5                   10                  15
Asp Gly Pro Gly Ile Arg Phe Ile Thr Phe Phe Gln Gly Cys Leu Met
                20                  25                  30
Arg Cys Leu Tyr Cys His Asn Arg Asp Thr Trp Asp Thr His Gly Gly
        35                  40                  45
Lys Glu Val Thr Val Glu Asp Leu Met Lys Glu Val Val Thr Tyr Arg
    50                  55                  60
His Phe Met Asn Ala Ser Gly Gly Gly Val Thr Ala Ser Gly Gly Glu
65                  70                  75                  80
Ala Ile Leu Gln Ala Glu Phe Val Arg Asp Trp Phe Arg Ala Cys Lys
                85                  90                  95
Lys Glu Gly Ile His Thr Cys Leu Asp Thr Asn Gly Phe Val Arg Arg
                100                 105                 110
Tyr Asp Pro Val Ile Asp Glu Leu Leu Glu Val Thr Asp Leu Val Met
            115                 120                 125
```

-continued

```
Leu Asp Leu Lys Gln Met Asn Asp Glu Ile His Gln Asn Leu Val Gly
    130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Pro Gly Trp Ser Asp
                165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
        195                 200                 205

Lys Trp Val Ala Met Gly Glu Glu Tyr Lys Leu Asp Gly Val Lys Pro
    210                 215                 220

Pro Lys Lys Glu Thr Met Glu Arg Val Lys Gly Ile Leu Glu Gln Tyr
225                 230                 235                 240

Gly His Lys Val Met Phe
                245
```

USE OF ENZYMES WHICH CATALYZE PYRUVATE SYNTHESIS FROM FORMATE AND ACETYL-COA AND BACTERIA EXPRESSING SAME

RELATED APPLICATIONS

This application is a National Phase of PCT Patent Application No. PCT/IL2014/051080 having International filing date of Dec. 10, 2014, which claims the benefit of priority under 35 USC § 119(e) of U.S. Provisional Patent Application No. 61/913,940 filed on Dec. 10, 2013. The contents of the above applications are all incorporated by reference as if fully set forth herein in their entirety.

SEQUENCE LISTING STATEMENT

The ASCII file, entitled 66256SequenceListing.txt, created on Jun. 2, 2016, comprising 9,116 bytes, submitted concurrently with the filing of this application is incorporated herein by reference.

FIELD AND BACKGROUND OF THE INVENTION

The present invention, in some embodiments thereof, relates to microorganisms which express enzymes which catalyze the conversion of formate and acetyl-CoA to pyruvate.

The concept of biorefineries has become a wide spread notion in the last decade. It relies on the premise that living organisms can and should be used to supply the increasing demand by humanity for specialized chemicals, including fuels, solvents, plastics, pharmaceuticals, etc. Today, most of these chemicals are derived, directly or indirectly, from fissile carbons. However, with the imminent depletion of these fossil carbons and the increase in atmospheric $CO_2$ it has become essential to find alternative sources for these important materials.

The suggested feedstocks for most of the proposed biorefineries are simple sugars, starch, or lingocellulosic biomass. While the latter alternative has an apparent advantage over the former by not-competing with human consumption needs, it still presents numerous difficulties, including a problematic fermentation technology and feedstock availability and transportation. A fascinating alternative feedstock would be electric current. Electrons can be shuttled from an electrode to living cells, providing the necessary reducing equivalents and energy to support autotrophic growth and electrosynthesis of desired commodities. Since electricity is widely available, microbial electrosynthesis can be spatially and temporally decoupled from energy production and can take place at any convenient location and time.

Microbial electrosynthesis can be especially useful for the renewable energy market. One major drawback of most renewable energy sources, including solar, wind, hydro and nuclear, is that they are hard to store in a convenient way. Microbial electrosynthesis of fuels can thus serve to address this problem efficiently, converting electrical energy to kinetically stable chemical bonds.

$CO_2$ can be directly reduced at the cathode (the electrons are derived from water splitting at the anode), providing organic compounds that can be used by living cells as a source of reducing equivalents, energy and even carbon. A diverse group of compounds can be produced in this manner. The production of simple alcohols, such as methanol, ethanol and propanol, hydrocarbons, such as methane and ethylene, or acids with more than one carbon, such as acetic acid and oxalic acid, has the advantage of supplying microbes with compounds relatively simple to metabolize and/or being rich in reducing equivalents. However, the electrocatalytic production of all of these compounds is generally inefficient (not specific to a single product and/or requiring high overpotential), requiring costly catalysts and/or supporting low current density. In contrast, there are two compounds that can be produced by direct reduction of $CO_2$ at relatively high efficiency (although lower than that of molecular hydrogen) and an acceptable current density: carbon monoxide and formic acid. Since carbon monoxide is a toxic and flammable gas with low solubility, formic acid, being readily soluble and of low toxicity, is a preferred mediator of electrons. In fact, a formate-based economy was recently proposed as an alternative to the hydrogen-based economy or methanol-based economy concepts.

In most organisms, glycolysis is the main route by which the cell obtains its biomass building blocks, as well as available energy (in the form of ATP), from sugars [1]. There are several natural variants of the glycolytic pathway, differing in their ATP yield, metabolic flux and sensitivity to external conditions [2-4]. However, all these alternatives share one feature in common: they produce stoichiometric amounts of pyruvate molecules from hexoses, pentoses and trioses. On the other hand, the faith of pyruvate changes depending on the organism and conditions. Under aerobic conditions or when other electron acceptors are available, pyruvate is mostly decarboxylated and oxidized—via either pyruvate dehydrogenase or pyruvate oxidase—to form acetyl-CoA, which feeds the TCA cycle. Other pyruvate molecules are used as biomass building blocks, either directly (e.g., valine biosynthesis) or through anaplerotic reactions (e.g., aspartate biosynthesis). When terminal electron acceptors are absent, requiring a redox-balanced fermentation, pyruvate is usually converted to lactate or ethanol, in a process which provides two ATP molecules per fermented hexose.

Mixed acid fermentation is a metabolic strategy which enables the cells to increase their ATP production from 2 to 3 molecules per hexose (e.g., [5-9]). In this redox-balanced process the enzyme pyruvate formate-lyase (PFL) cleaves pyruvate to acetyl-CoA and formate. Half of the acetyl-CoA molecules are then reduced to ethanol, while the other half is secreted as acetate, providing an extra ATP. PFL operates in numerous organisms [10], prokaryotes [6,7,11-15] as well as eukaryotes [16-18]. The most studied PFL variant is from the γ-proteobacterium *Escherichia coli* (e.g., [19-22]).

In *E. coli*, PFL is encoded by the pflB gene and is active as a homodimer of 85 kDa polypeptides [23]. Pyruvate cleavage takes place via a radical mechanism, which involves a glycyl radical on $G^{734}$ of PFL [24-26]. Pyruvate formate-lyase activating enzyme (PFL-AE)—encoded by the pflA gene in *E. coli*—generates the stable and catalytically essential glycyl radical [27,28]. PFL-AE performs this remarkable feat by using an iron-sulfur cluster and S-adenosylmethionine, thus placing it among the AdoMet radical superfamily of enzymes [28].

The glycyl radical is susceptible to destruction by oxygen, which results in irreversible cleavage of the polypeptide and inactivation of PFL [29,30]. However, previous studies have shown that *E. coli* cells grown under microaerobic conditions produce a significant amount of formate, indicating that PFL retains its activity in the presence of low level of oxygen [21,31,32]. The product of the yfiD gene was shown to reactivate PFL in the presence of oxygen by replacing its fragmented part [32,33].

While the PFL reaction was shown to be reversible in-vitro ($\Delta_r G'^o \approx -10$ kJ/mol at pH 7.5 and ionic strength of 0.2 M), catalyzing pyruvate formation at a non-negligible rate ($k_{cat} > 4$ s$^{-1}$ [37]), the significance of this backward reaction was never explored in-vivo.

PCT International Application No. PCT/IL2013/050643 teaches formatotrophic bacteria that use the reductive glycine pathway.

SUMMARY OF THE INVENTION

According to an aspect of some embodiments of the present invention there is provided an isolated microorganism being genetically modified to express pyruvate formate lyase (PFL) or 2-ketobutyrate formate lyase, wherein acetyl-CoA of the microorganism is converted to pyruvate in the presence of formate in a single step reaction, wherein the net flux of the reaction is in the direction of pyruvate synthesis.

According to an aspect of some embodiments of the present invention there is provided an isolated microorganism being genetically modified to express pyruvate formate lyase (PFL) or 2-ketobutyrate formate lyase, wherein acetyl-CoA of the microorganism is converted to pyruvate in the presence of formate in a single step reaction, wherein the net flux of the reaction is in the direction of pyruvate synthesis wherein the microorganism does not express isocitrate lyase and/or malate synthase.

According to an aspect of some embodiments of the present invention there is provided a system for culturing the microorganism described herein and an electrode for providing electrons to generate formate from $CO_2$.

According to an aspect of some embodiments of the present invention there is provided a cell culture comprising the isolated microorganism described herein and a medium suitable for propagation of the microorganism.

According to an aspect of some embodiments of the present invention there is provided a cell culture, comprising isolated microorganism being genetically modified to express an enzyme of a reaction which converts acetyl-CoA of the microorganism to pyruvate in the presence of formate in a single step, and a medium comprising an amount of acetate and/or formate which favors the net flux of the reaction to be in the direction of pyruvate synthesis.

According to an aspect of some embodiments of the present invention there is provided a method of generating a biofuel comprising culturing the microorganism described herein under conditions that allow for biofuel formation, thereby generating the biofuel.

According to an aspect of some embodiments of the present invention there is provided a method of generating a human polypeptide comprising culturing the microorganism described herein under conditions that allow for expression of the human polypeptide, thereby generating the human polypeptide.

According to an aspect of some embodiments of the present invention there is provided a method of scavenging acetate from an acetate-containing medium comprising contacting the microorganism described herein with the medium, thereby scavenging the acetate from the acetate-containing medium.

According to an aspect of some embodiments of the present invention there is provided a method of scavenging formate from a formate-containing medium comprising contacting the microorganism described herein with the medium, thereby scavenging the formate from the formate-containing medium.

According to some embodiments of the invention, the enzyme comprises pyruvate formate lyase (PFL).

According to some embodiments of the invention, the enzyme comprises 2-ketobutyrate formate lyase.

According to some embodiments of the invention, the pyruvate formate lyase is encoded by a gene selected from the group consisting of pflB, pflD and ybiW.

According to some embodiments of the invention, the isolated microorganism further expresses a polypeptide which activates the pyruvate formate lyase enzyme.

According to some embodiments of the invention, the microorganism does not expressing isocitrate lyase.

According to some embodiments of the invention, the microorganism has a doubling time when cultivated in a medium comprising formate of between 1-20 hours.

According to some embodiments of the invention, the microorganism has a doubling time when cultivated in a medium comprising formate of between 3-12 hours.

According to some embodiments of the invention, the medium further comprises acetate.

According to some embodiments of the invention, the microorganism is capable of generating an internal source of acetyl-CoA.

According to some embodiments of the invention, the microorganism is formatotrophic.

According to some embodiments of the invention, the microorganism expresses at least one of the enzymes selected from the group consisting of pyruvate carboxylase, malate dehydrogenase, malate-CoA ligase and malyl-CoA lyase.

According to some embodiments of the invention, the microorganism expresses each of pyruvate carboxylase, malate dehydrogenase, malate-CoA ligase and malyl-CoA lyase.

According to some embodiments of the invention, the microorganism expresses at least one of the enzymes selected from the group consisting of PEP synthetase, phosphopyruvate hydratase, phosphoglyceromutase, 3-phosphoglycerate kinase, glyceraldehyde 3-phosphate dehydrogenase, triose phosphate isomerase, fructose bisphosphate aldolase, fructose bisphosphatase, transketolase, transaldolase, ribulose-phosphate 3-epimerase, ribose 5-phosphate isomerase A, phosphoketolase and phosphate acetyltransferase.

According to some embodiments of the invention, the microorganism expresses each of PEP synthetase, phosphopyruvate hydratase, phosphoglyceromutase, 3-phosphoglycerate kinase, glyceraldehyde 3-phosphate dehydrogenase, triose phosphate isomerase, fructose bisphosphate aldolase, fructose bisphosphatase, transketolase, transaldolase, ribulose-phosphate 3-epimerase, ribose 5-phosphate isomerase A, phosphoketolase and phosphate acetyltransferase.

According to some embodiments of the invention, the microorganism is autotrophic.

According to some embodiments of the invention, the microorganism is chemotrophic.

According to some embodiments of the invention, the microorganism is phototrophic.

According to some embodiments of the invention, the microorganism is methyltrophic.

According to some embodiments of the invention, the microorganism is cultivated on a fuel selected from the group consisting of methane, methanol, methylamine and carbon monoxide.

According to some embodiments of the invention, the microorganism is aerobic.

According to some embodiments of the invention, the microorganism is anaerobic.

According to some embodiments of the invention, the microorganism is a bacterium.

According to some embodiments of the invention, the microorganism is a gram positive bacterium.

According to some embodiments of the invention, the microorganism is a gram negative bacterium.

According to some embodiments of the invention, the bacterium is selected from the group consisting of *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus,* and *Zymomonas*.

According to some embodiments of the invention, the microorganism is bacterium comprises *Escherichia*.

According to some embodiments of the invention, the microorganism is incapable of transporting and utilizing sugar.

According to some embodiments of the invention, the microorganism expresses at least one of the enzymes selected from the group consisting of phosphoglyceromutase, isocitrate lyase and phosphogluconate dehydratase.

According to some embodiments of the invention, the microorganism is a yeast.

According to some embodiments of the invention, the yeast comprises *S. cervavisciae*.

According to some embodiments of the invention, the microorganism is a fungus.

According to some embodiments of the invention, the fungus is selected from *Aspergillus, Candida, Chlamydomonas, Chrysosporium, Cryotococcus, Fusarium, Kluyveromyces, Neotyphodium, Neurospora, Penicillium, Pichia, Saccharomyces, Trichoderma* and *Xanthophyllomyces*.

According to some embodiments of the invention, the microorganism is an alga.

According to some embodiments of the invention, the microorganism is genetically modified to express a human polypeptide.

According to some embodiments of the invention, the human polypeptide is selected from the group consisting of an antibody, insulin, interferon, growth hormone, erythropoietin, growth hormone, follicle stimulating hormone, factor VIII, low density lipoprotein receptor (LDLR) alpha galactosidase A and glucocerebrosidase.

According to some embodiments of the invention, the microorganism is capable of producing a biofuel.

According to some embodiments of the invention, the biofuel is selected from the group consisting of ethanol, propanol, isobutanol and n-butanol.

According to some embodiments of the invention, the biofuel is selected from the group consisting of an alcohol, an alkene, an alkane, a lipid or a polysaccharide.

According to some embodiments of the invention, the medium comprises an amount of acetate and/or formate which favors the net flux of the reaction to be in the direction of pyruvate synthesis.

According to some embodiments of the invention, the method further comprises collecting the biofuel.

According to some embodiments of the invention, the method further comprises isolating the human polypeptide.

According to some embodiments of the invention, the acetate-containing medium further comprises formate.

According to some embodiments of the invention, the formate is supplemented to the medium from an external source.

According to some embodiments of the invention, the microorganism endogenously generates the formate.

According to some embodiments of the invention, the microorganism is incapable of transporting and utilizing sugar.

According to some embodiments of the invention, the microorganism does not express isocitrate lyase.

According to some embodiments of the invention, the formate-containing medium further comprises acetate.

According to some embodiments of the invention, the acetate is supplemented to the medium from an external source.

According to some embodiments of the invention, the microorganism endogenously generates the acetate.

According to some embodiments of the invention, the microorganism is incapable of transporting and utilizing sugar.

According to some embodiments of the invention, the microorganism does not express at least one of the enzymes selected from the group consisting of phosphoglyceromutase and phosphogluconate dehydratase.

According to some embodiments of the invention, the microorganism is selected from the group consisting of a bacterium, a yeast, a fungus and an alga.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
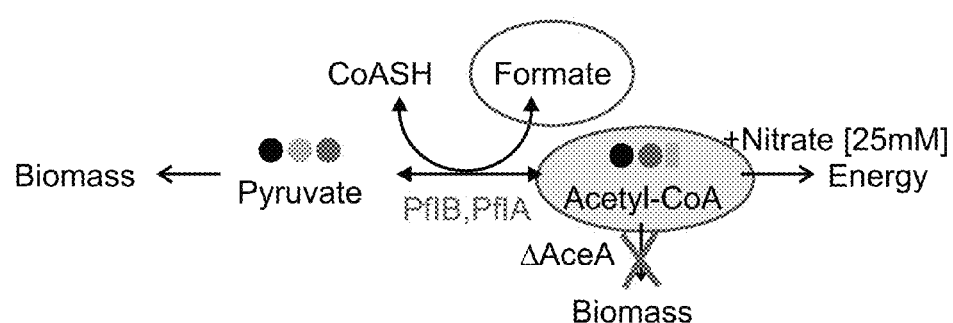
Figure 1B:
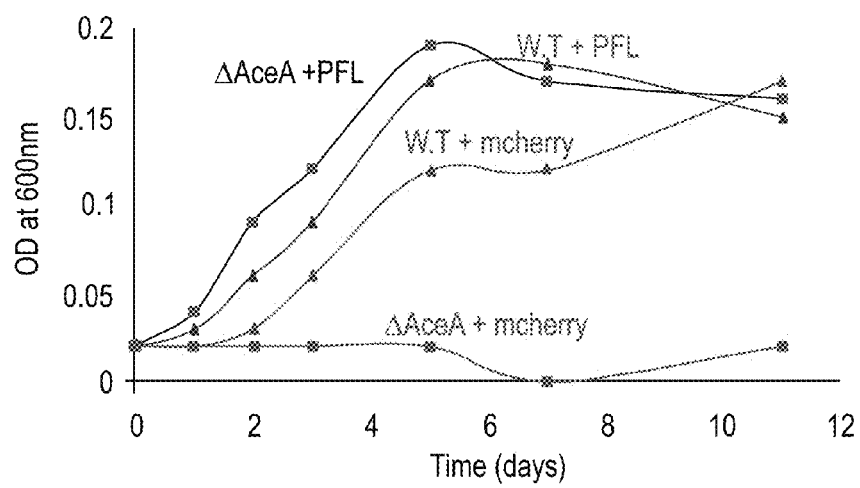

FIGS. 1A-B illustrates that overexpression of PFL rescues growth on acetate of a ΔaceA mutant of *E. coli* (in which aceA encodes for isocitrate lyase). (A) Schematics of a PFL-dependent growth of a ΔaceA mutant. Gene deletions are marked in an 'X' sign, carbon sources are marked as blue circles, and the overexpressed enzymes are shown in red. (B) Growth assays for a ΔaceA mutant in which either PFL or mcherry (as a control) were overexpressed. Note that even in the case of mcherry overexpression, native PFL is still present, but at a suboptimal level.

Figure 2:
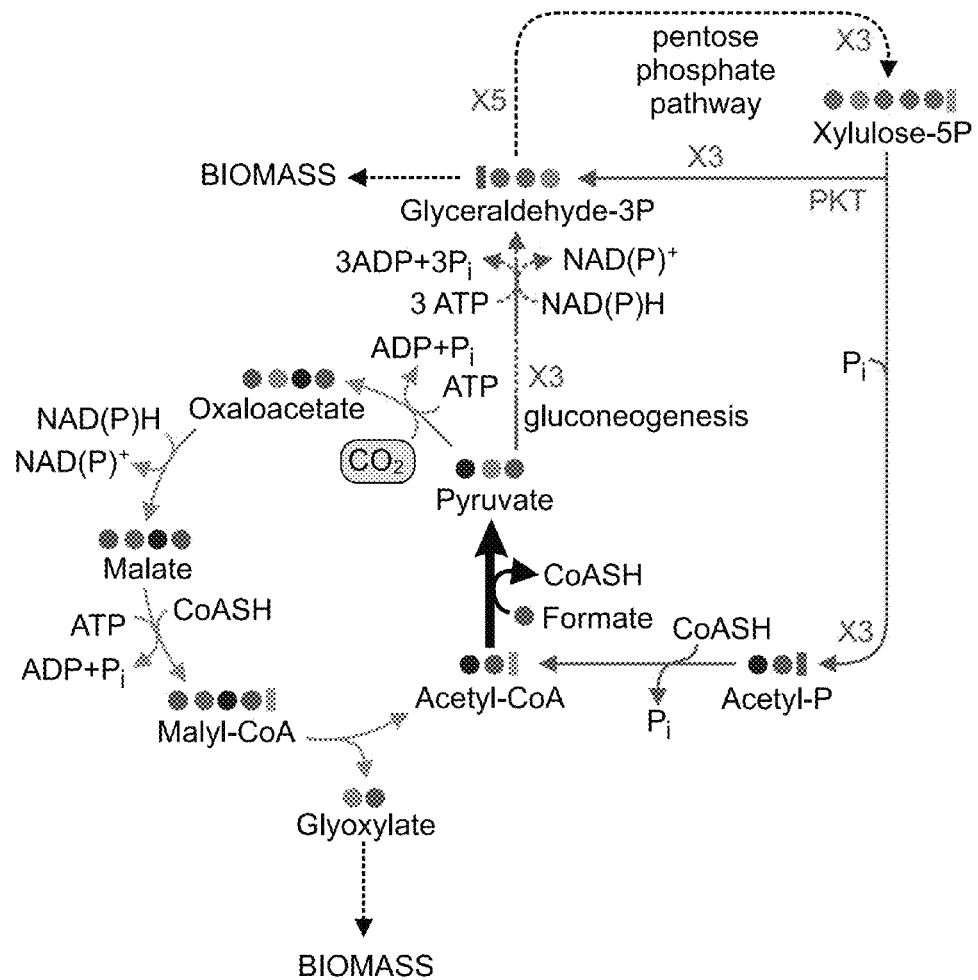

FIG. 2 is a diagram schematically illustrating alternative PFL-dependent formate assimilation pathways.

Figure 3:
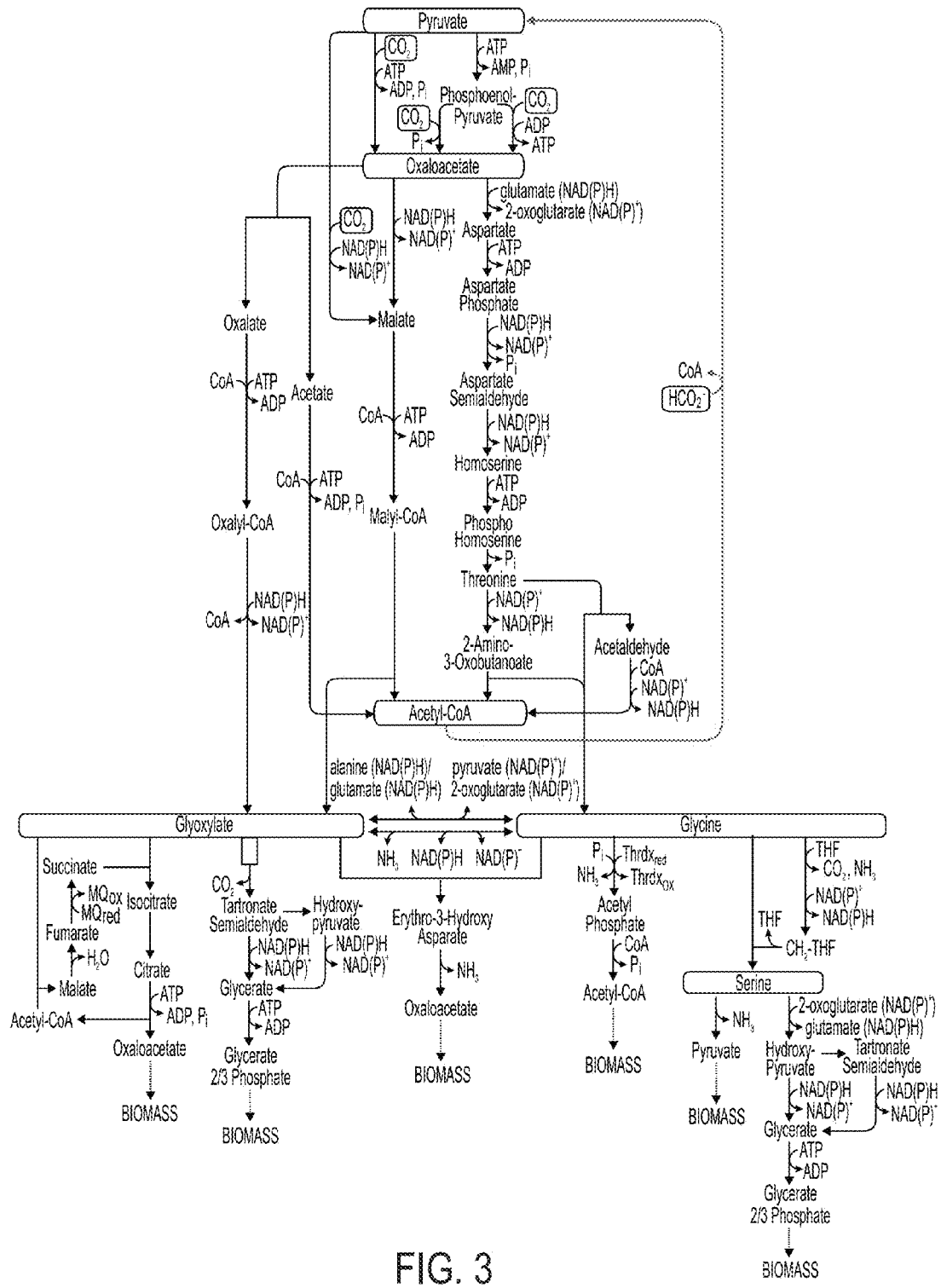

FIG. 3 is a diagram illustrating the structure of the anaplerotic PFL-dependent formate assimilation pathways.

Figure 4:
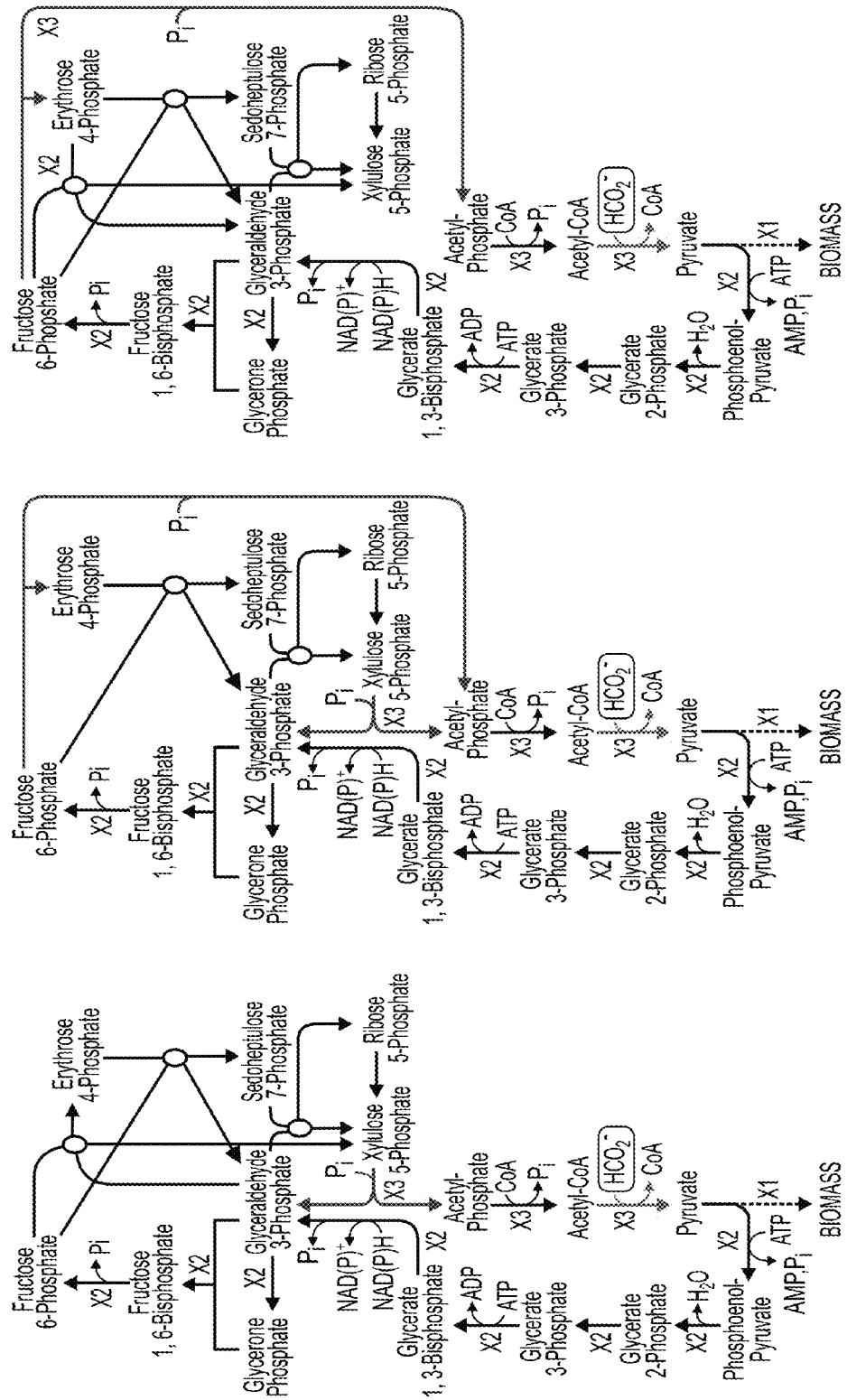
Figure 4:
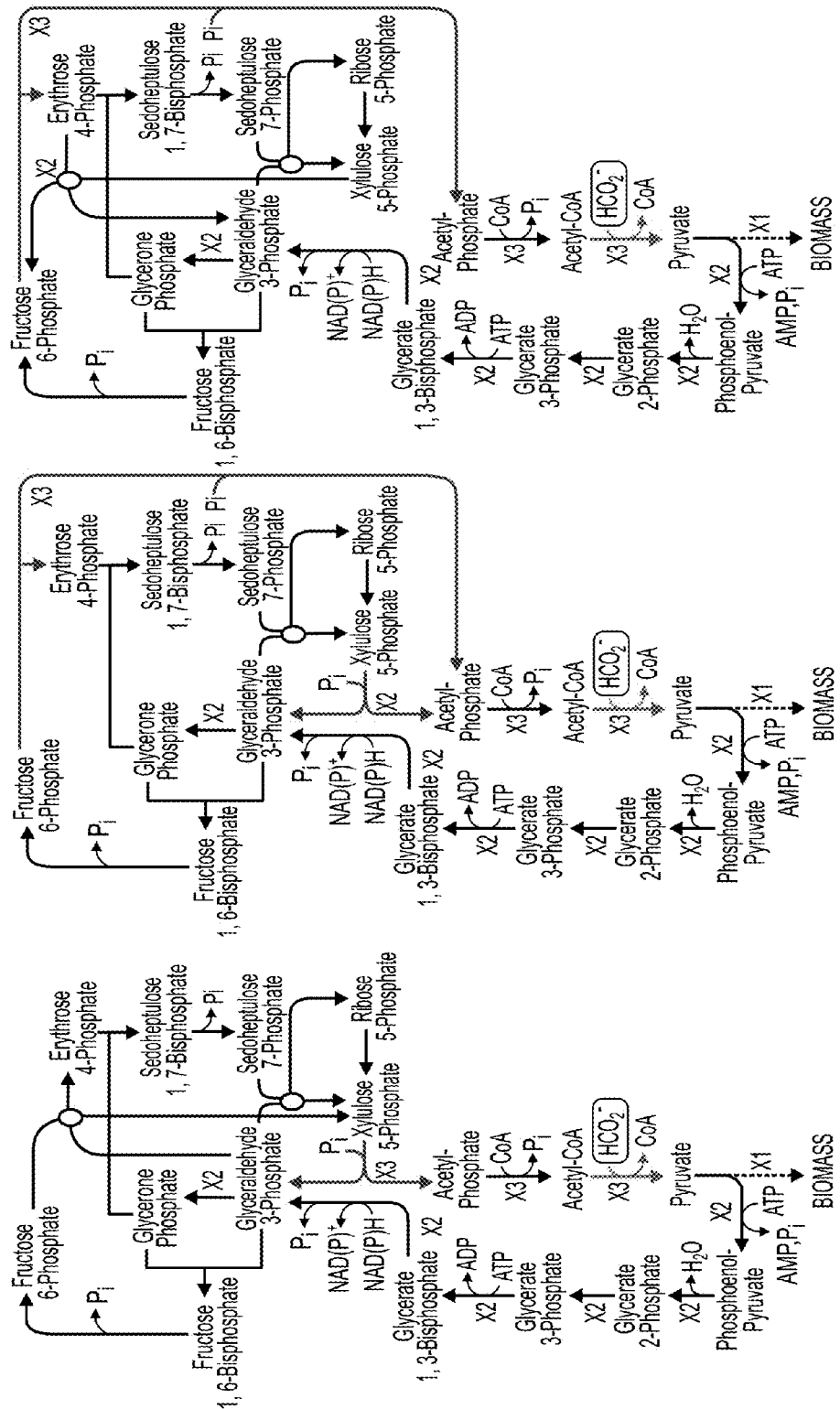

FIG. 4 is a diagram illustrating the structure of the pentose-phosphate-glconeogenic PFL-dependent formate assimilation pathways.

DESCRIPTION OF SPECIFIC EMBODIMENTS OF THE INVENTION

The present invention, in some embodiments thereof, relates to microorganisms which express enzymes which catalyze the conversion of formate and acetyl-CoA to pyruvate.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Electrosynthesis has recently received much attention as being a promising approach for use of a renewable energy for the production of commodities by living cells. Several techniques were proposed to mediate the transfer of electrons from the cathode to living cells. Of these, the electroproduction of formate as a mediator seems to be especially interesting: formate is readily soluble, of low toxicity and can be produced at high efficiency and at reasonable current density.

There are numerous metabolic pathways that, once expressed in a microorganism, can potentially support formatotrophic growth. The present inventors have now uncovered that microorganisms can be genetically modified such that they can assimilate formate via a pyruvate-formate-lyase (PFL) dependent mechanism.

The present inventors demonstrated the ability to produce such bacteria by engineering a ΔaceA (a deletion in isocitrate lyase) strain of bacteria to express PFL. This bacteria was able to grow on a mixture of acetate and formate (FIG. 1B).

Such formate assimilation pathways can potentially support carbon fixation and autotrophic growth in the microorganisms when coupled with $CO_2$ reducing formate dehydrogenase and an external source of reducing power. Alternatively, the formate assimilation pathways can support the assimilation of other reduced C1 compounds (e.g. methane, methanol, methylamine or formaldehyde). As these compounds can be converted in the microorganisms to formate, their assimilation can be engineered to be PFL-dependent. Hence, the above formate assimilation pathways can replace the native ribulose monophosphate, dehydroacetone and serine pathways, which support the assimilation of reduced C1 compounds in methylotrophic organisms.

In addition, microorganisms which assimilate acetyl-CoA via a pyruvate-formate-lyase (PFL) dependent mechanism can be used to support the conversion of C2 to C3 compounds, thereby circumventing the use of intricate pathways such as the glyoxylate shunt, the ethylmalonyl-CoA pathway or the methylaspartate cycle.

Furthermore, microorganisms that have been genetically modified to carry out the reverse reaction of PFL can be important in scavenging acetate that accumulates in the fermentation medium. Accumulation of acetate can hamper the fermentation process, as it inhibits many central metabolic processes.

To implement this strategy efficiently, the present inventors contemplate engineering a dedicated microorganism strain in which the sugar transport and utilizing genes thereof are deleted or rendered non-functional. Further, the endogenous isocitrate lyase and malate synthease enzymes may be deleted and the PFL enzyme may be overexpressed. This strain will be dependent on acetate and formate for its growth and will not compete with the primary fermenting strains for the sugars.

Just as in the case of acetate, accumulation of formate in the fermentation medium (e.g., during mixed acid fermentation) can be deleterious for microbial growth. Accordingly, the present inventors contemplate microorganism which are genetically engineered to carry out the reverse reaction of PFL and use them to scavenge formate from the medium when acetate is provided externally or internally.

Thus, according to one aspect of the present invention there is provided an isolated microorganism being genetically modified to express an enzyme which converts acetyl coA of the microorganism to pyruvate in the presence of formate in a single step, wherein the net flux of the reaction is in the direction of pyruvate synthesis.

As used herein, the term "microorganism" refers to any organism of microscopic size. Non-limiting examples of microorganisms as the term is used herein include both prokaryotic and eukaryotic microorganisms, such as bacteria, archae, protozoan, fungi, molds, yeasts, algae etc. The microorganism may be aerobic or anaerobic.

The organisms can be fermentative organisms. Exemplary microorganisms include, for example, *Clostridium* (e.g., *C. acetobutylicum*, *C. Beijerinckii*, *C. saccharoperbutylacetonicum*, *C. saccharobutylicum*, *C. aurantibutyricum*, *C. tetanomorphum*), *Zymomonas*, *Escherichia* (e.g., *E. coli*), *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Pichia*, *Candida*, *Hansenula*, *Zymomonas* and *Saccharomyces*, e.g., *Saccharomyces cerevisiae*, *Saccharomyces carlsbergensis*, *Kluyveromyces lactis*, *Saccharomyces lactis*.

The bacteria may be those which are useful in the food industry. For example lactic Acid Bacteria (LAB) play an essential role in the preservation, taste and texture of cheese, yogurt, sausage, sauerkraut and a large variety of traditional indigenous fermented foods.

As used herein, the expression "lactic acid bacterium" refers to a group of gram-positive, microaerophilic or anaerobic bacteria having in common the ability to ferment sugars and citrate with the production of acids including lactic acid as the predominantly produced acid, acetic acid, formic acid and propionic acid. The industrially most useful lactic acid bacteria are found among *Lactococcus* species, *Streptococcus* species, *Lactobacillus* species, *Leuconostoc* species, *Oenococcus* species and *Pediococcus* species. In the dairy industry, the strict anaerobes belonging to the genus *Bifidobacterium* is generally included in the group of lactic acid bacteria as these organisms also produce lactic acid and are used as starter cultures in the production of dairy products.

Thus, the present invention contemplates food products which comprise such bacteria.

Bacteria may be gram positive or gram negative. Examples of bacteria which are contemplated by the present invention include, but are not limited to *Agrobacterium*, *Alicyclobacillus*, *Anabaena*, *Anacystis*, *Arthrobacter*, *Azo-* bacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus, and Zymomonas.

Examples of fungi contemplated by the present invention include, but are not limited to Aspergillus, Candida, Chlamydomonas, Chrysosporium, Cryotococcus, Fusarium, Kluyveromyces, Neotyphodium, Neurospora, Penicillium (e.g. P. chrysogenum), Pichia, Saccharomyces, Trichoderma and Xanthophyllomyces.

Examples of algae contemplated by the present invention include, but are not limited to a diatom or a cyanobacterium.

The diatom may be a microalgae of the class Coscinodiscophyceae, Fragilariophyceae or Bacillariophyceae.

The cyanobacterium can include, for example, Botryococcus braunii, Chlorella, Dunaliella tertiolecta, Gracilaria, Pleurochrysis carterae, Sargassum or Ulva.

The microorganism may be methylotrophic—i.e. is capable of growing on organic C1 compounds as their sole carbon, reducing power and energy source. Examples of such compounds include methane, methanol, methylamine and carbon monoxide.

According to a particular embodiment, the methylotrophic microorganism is formatotrophic—i.e. uses formate as a carbon, reducing power and energy source. It will be appreciated that the formatotrophic organisms of the present invention may also be capable of growing on additional carbon sources—such as glucose, glycerol cellulose, acetate, butyrate, lactate, propionate, or valerate.

According to another embodiment, the microorganism is autotrophic. One type of autotrophic microorganism is a phototrophic organism (one which requires light to get the reducing power and energy for carbon dioxide fixation). The electron source for photosynthesis may be for example, water, hydrogen sulfide, elemental sulfur or ferrous ion ($Fe^{2+}$).

Another type of autotrophic microorganism is a chemotrophic microorganism (one which requires an external electron source [e.g., molecular hydrogen, carbon monoxide (CO), hydrogen sulfide ($H_2S$), elemental sulfur (S), sulfite ($SO_3^{2-}$), phosphite ($PO_3^{2-}$), ammonia ($NH_4^+$), nitrite ($NO_2^{2-}$), ammonium hydroxide ($NH_2OH$), ferrous ion ($Fe^{2+}$), $Mn^{2+}$ ion] to get the reducing power and energy for carbon dioxide fixation). Possible terminal electron acceptors include molecular oxygen, carbon dioxide ($CO_2$), sulfate ($SO_4^{2-}$), elemental sulfur (S), nitrate ($NO_3^{2-}$), ferric ion ($Fe^{3+}$).

The microorganisms of the present invention express, either naturally or are genetically engineered so as to express an enzyme which converts acetyl-CoA of the microorganism to pyruvate in the presence of formate in a single step, wherein the net flux of the reaction is in the direction of pyruvate synthesis.

The term "enzyme" as used herein refers to a "catalytically functional biomolecule," which includes both whole native (or native-size) molecules and derivatives (e.g. genetic modifications) thereof.

The phrase "in a single step" as used herein, refers to the ability of the enzyme to catalyze the reaction without the formation of an intermediary product.

Examples of such enzymes include, but are not limited to pyruvate formate lyase (PFL; EC number 2.3.1.54, encoded in E. coli by the pflB gene, e.g. Accession Numbers: EG10701 (EcoCyc), b0903, ECK0894); 2-ketobutyrate formate-lyase, (encoded by the tdcE gene, Accession Numbers: G7627 (EcoCyc), b3114, ECK3103) and the proteins encoded by pflD and ybiW genes (see for example Zhu et al., (2004) Appl Microbiol Biotechnol 64: 367-375), the contents of which are incorporated herein by reference.

Thus an enzyme of the present invention also refers to homologs and other modifications including additions or deletions of specific amino acids to the sequence (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to the amino acid sequence as set forth in SEQ ID NO: 1, as determined using BlastP software of the National Center of Biotechnology Information (NCBI) using default parameters). The homolog may also refer to an ortholog, a deletion, insertion, or substitution variant, including an amino acid substitution, thereof and biologically active polypeptide fragments thereof.

Since the PFL enzyme is typically inactive and requires a stable and catalytically essential glycyl radical on $G^{734}$ the present invention further contemplates expressing a pyruvate formate-lyase activating enzyme (PFL-AE; EC number 1.97.1.4) in the microorganism. Examples of PFL-AEs are those encoded by pflA gene or the pflC gene or the YjjW gene.

The PFL-AE of the present invention also refers to homologs and other modifications including additions or deletions of specific amino acids to the sequence (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to the amino acid sequence as set forth in SEQ ID NO: 2, as determined using BlastP software of the National Center of Biotechnology Information (NCBI) using default parameters). The homolog may also refer to an ortholog, a deletion, insertion, or substitution variant, including an amino acid substitution, thereof and biologically active polypeptide fragments thereof.

Nucleic acid sequences encoding the enzymes and enzyme activating proteins of some embodiments of the invention may be optimized for expression for a particular microorganism. Examples of such sequence modifications include, but are not limited to, an altered G/C content to more closely approach that typically found in the microorganism species of interest, and the removal of codons atypically found in the microorganism species commonly referred to as codon optimization.

The phrase "codon optimization" refers to the selection of appropriate DNA nucleotides for use within a structural gene or fragment thereof that approaches codon usage within the microorganism of interest. Therefore, an optimized gene or nucleic acid sequence refers to a gene in which the nucleotide sequence of a native or naturally occurring gene has been modified in order to utilize statistically-preferred or statistically-favored codons within the microorganism. The nucleotide sequence typically is examined at the DNA level and the coding region optimized for expression in the microorganism species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed genes, followed by a calculation of the average squared deviation. The formula used is: 1

SDCU=n=1 N [(Xn−Yn)/Yn]2/N, where Xn refers to the frequency of usage of codon n in highly expressed genes, where Yn to the frequency of usage of codon n in the gene of interest and N refers to the total number of codons in the gene of interest.

One method of optimizing the nucleic acid sequence in accordance with the preferred codon usage for a particular cell type is based on the direct use, without performing any extra statistical calculations, of codon optimization tables such as those provided on-line at the Codon Usage Database through the NIAS (National Institute of Agrobiological Sciences) DNA bank in Japan (www(dot)kazusa(dot)or(dot)p/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, *E. coli*), a naturally-occurring nucleotide sequence encoding a protein of interest can be codon optimized for that particular species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular species. Therefore, codon optimization of the native nucleotide sequence may comprise determining which codons, within the native nucleotide sequence, are not statistically-favored with regards to a particular plant, and modifying these codons in accordance with a codon usage table of the particular species to produce a codon optimized derivative. A modified nucleotide sequence may be fully or partially optimized for microorganism codon usage provided that the protein encoded by the modified nucleotide sequence is produced at a level higher than the protein encoded by the corresponding naturally occurring or native gene. Construction of synthetic genes by altering the codon usage is described in for example PCT Patent Application No. 93/07278.

To express the enzymes of the present invention using recombinant technology, polynucleotides encoding the enzymes may be ligated into a nucleic acid expression vector, under the transcriptional control of a cis-regulatory sequence (e.g., promoter sequence) suitable for directing constitutive or inducible transcription of the enzymes in the microorganism.

Thus, the present invention contemplates isolated polynucleotides encoding the enzymes of the present invention.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhancers) and transcription and translation terminators (e.g., polyadenylation signals).

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Exemplary bacterial based expression systems are disclosed in Baneyx et al., Current Opinion in Biotechnology, 1999; 10, 411-421 and Macrides et al, Microbiol Rev 1996, 60: 512-538, incorporated herein by reference.

The microorganisms may be transformed stably or transiently with the nucleic acid constructs of the present invention. In stable transformation, the nucleic acid molecule of the present invention is integrated into the microorganism genome and as such it represents a stable and inherited trait. In transient transformation, the nucleic acid molecule is expressed by the cell transformed but it is not integrated into the genome and as such it represents a transient trait.

As mentioned, the net flux of the reaction in the microorganism is in the direction of pyruvate synthesis.

It will be appreciated that enzymes such as pyruvate formate lyase catalyze the reaction of acetyl-CoA and formate to generate pyruvate and the reverse reaction of pyruvate degradation into acetyl-CoA and formate. The conditions of the reaction are such that the net flux of the reaction is in the direction of pyruvate synthesis. One way of manipulating the conditions is by increasing the concentration of formate in the medium. Another way of manipulating the conditions to favor pyruvate synthesis is by increasing the amount of acetyl-CoA available to the microorganism. Yet another alternative is to provide a strong sink for pyruvate, i.e. pyruvate is consumed at a high rate by other cellular reactions.

The source of the acetyl-CoA which the microorganism requires may be acetate presented in the medium (e.g., 0.01%-10% sodium acetate, or more preferably 0.1%-5%). Alternatively, the microorganism may be capable of generating acetyl-CoA without an external source of acetate.

In order to generate an internal source of acetyl-CoA there are two general structure types a PFL-dependent formate assimilation pathway can adopt. The "anaplerotic" structure (shown in purple in FIG. 2) involves the carboxylation of the PFL-derived pyruvate to oxaloacetate (via pyruvate carboxylase or alternatively PEP carboxylase) and its further reduction to malate. Malate is then ligated with coenzyme-A to form malyl-CoA which is cleaved to recycle the acetyl-CoA and produce glyoxylate on which the cell can grow. In the "pentose-phosphate-glconeogenic" structure (shown in orange in FIG. 2) the PFL-derived pyruvate is reduced to glyceraldehyde 3-phosphate via the native glconeogenic pathway. The native pentose phosphate pathway then converts glyceraldehyde 3-phosphate to xylulose 5-phosphate which is cleaved by the enzyme phosphoketolase (marked as 'PKT' in FIG. 2) to glyceraldehyde 3-phosphate and acetyl phosphate Acetyl phosphate is converted to acetyl-CoA by the endogenous phosphate acetyltransferase enzyme, thus completing the cycle. Alternatively, phosphoketolase can be used to cleave fructose 6-phosphate (instead of xylulose 5-phosphate).

There are several variants of the "anaplerotic" structure described herein above as shown in FIG. 3. These pathways may be referred to as the PFL-APOG pathways, where APOG stands for Acetyl-CoA-Pyruvate-Oxaloacetae-Glyoxylate/Glycine, the common metabolites in almost all of these pathways.

For a microorganism to utilize the anaplerotic structure of the PFL-dependent formate assimilation pathway, it may express the following enzymes:

Pyruvate formate lyase (EC number 2.3.1.51), pyruvate formate lyase activating enzyme (EC number 1.97.1.4), pyruvate carboxylase (EC number 6.4.1.1), malate dehydrogenase (EC number 1.1.1.37), malate-CoA ligase (EC number 6.2.1.9) and malyl-CoA lyase (EC number 4.1.3.24).

It will be appreciated that if the microorganism does not endogenously express one or a combination of the enzymes noted above, the present invention contemplates genetic modification of the microorganism such that it expresses each of the above mentioned enzymes (or alternatives thereto) such that it is capable of utilizing the pathway (i.e. recombinant expression). Orthologs and paralogs of the above enzymes, as well as enzymes catalyzing the same activity as the above enzymes, can be used instead of the above mentioned enzymes. Specifically, any enzyme showing pyruvate formate lyase activity can be used instead of pflB and any enzyme that can activate pyruvate formate lyase can be used instead of pflA.

There are several variants of the "pentose-phosphate-gluconeogenic" structure as shown in FIG. 4. These variants are referred to herein as the PFL-PKT pathways, emphasizing the common enzymes in all of these pathways (PKT stands for phosphoketolase). Other formate assimilation pathways utilizing PFL and PKT pathways, apart from those shown in FIG. 4, can be envisioned, including different wiring of the pentose phosphate pathway and cleavage of other sugars by PKT.

For a microorganism to utilize the pentose-phosphate-gluconeogenic structure of the PFL-dependent formate assimilation pathway, it may express the following enzymes:

Pyruvate formate lyase (EC number 2.3.1.51), pyruvate formate lyase activating enzyme (EC number 1.97.1.4), PEP synthetase (EC number 2.7.92), phosphopyruvate hydratase (EC number 4.2.1.11), phosphoglyceromutase (EC number 5.4.2.11), 3-phosphoglycerate kinase (EC number 2.7.2.3), glyceraldehyde 3-phosphate dehydrogenase (EC number 1.2.1.12), triose phosphate isomerase (EC number 5.3.1.1), fructose bisphosphate aldolase (EC number 4.1.2.13), fructose bisphosphatase (EC number 3.1.3.11), transketolase (EC number 2.2.1.1), transaldolase (EC number 2.2.1.2), ribulose-phosphate 3-epimerase (EC number 5.1.3.1), ribose 5-phosphate isomerase A (EC number 5.3.1.6), phosphoketolase (EC number 4.1.2.9) and phosphate acetyltransferase (EC number 2.3.1.8).

It will be appreciated that if the microorganism does not endogenously express one or a combination of the enzymes noted above, the present invention contemplates genetic modification of the microorganism such that it expresses each of the above mentioned enzymes (or alternatives thereto) such that it is capable of utilizing the pathway. Orthologs and paralogs of the above enzymes, as well as enzymes catalyzing the same activity as the above enzymes, can be used instead of the above mentioned enzymes. Specifically, any enzyme showing pyruvate formate lyase activity can be used instead of pflB and any enzyme that can activate pyruvate formate lyase can be used instead of pflA.

In order to ensure that the microorganism utilizes the PFL enzyme for pyruvate synthesis, and does not rely on the endogenous glyoxylate shunt, the present invention contemplates microorganism strains in which the gene encoding for isocitrate lyase (aceA) and/or malate synthase is deleted, or the activity of isocitrate lyase or malate synthase is downregulated.

Methods of deleting genes from the chromosome of microorganisms are known to those of skill in the art and include homologous recombination, knock out techniques, RNAi etc.

The microorganisms of this aspect of the present invention are typically cultivated under effective conditions in a medium that supports their growth and allows expression of the enzymes described herein. Thus, for example the medium may comprise formate (e.g., 0.1%-1% sodium formate). Typically, the medium also comprises an electron acceptor such as nitrate, sulfate or oxygen at low levels (1-5%). The medium may also comprise appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

It will be appreciated that until the microorganism is transformed from being a heterotrophic microorganism to a formatotrophic microorganism or autotrophic microorganism, the microorganism is cultured in a culture medium comprising other carbon sources such as glucose or glycerol.

Following generation of the microorganisms as described herein, preferably they are selected by growing (i.e. culturing) on a particular substrate. Preferably, the microorganisms are grown for at least one day, at least two days, at least three days, at least one week, at least one month, at least three months wherein any viable cells remaining after such time are the selected microorganism.

Thus, for example in the case of generating a formatotrophic microorganism, the microorganism should be cultivated in a culture medium comprising formate as the carbon source. In the case of an autotrophic microorganism, the microorganism should be cultivated in a culture medium comprising carbon dioxide as the carbon source and an external electron source as further described herein above.

The formate which is used may come from any source—e.g., sodium formate, potassium formate, formic acid or formic acid anhydride etc.

Alternatively, and/or additionally, the formate may be generated using electricity. $CO_2$ can be directly reduced at the cathode (the electrons are derived from water splitting at the anode, for example) to generate formate at relatively high efficiency.

In order to generate the formate for use by the microorganism, the microorganism is placed in a bioreactor in a fluid (e.g., water). The cathode may optionally be placed inside the bioreactor in contact with the microorganism. Alternatively, the cathode may be placed in a separate container to the bioreactor and the formate may be channeled to the chamber comprising the microorganism. The fluid may contain other elements required by the microorganism for growth including for example salts, minerals, metals and other nutrients, such as vitamins.

Examples of such bioreactors and further methods are provided in Li et al. Science, 2012, Vol 335, page 1596, Rabaey et al, Current Opinion in Biotechnology, 2011, 22: 371-377; Lovley et al., Current Opinion in Biotechnology, 2011, 22: 441-448; Lovley D. R., Environmental microbiology reports, 2011, 3(1), 27-35; Nevin et al., Microbiology, May/June 2010 Volume 1 Issue 2; Rabaey et al., Applied and Industrial Microbiology, Nature Reviews, October 2010, Volume 8, page 706-716; each of which are incorporated herein by reference.

The electrodes may be fabricated from such conductive polymers and metallic materials including indium tin oxide (ITO), graphite, platinum and silver.

Thus, a system is contemplated for the microorganism described herein and an electrode for providing electrons to generate formate. The system may further comprise mechanism(s) for separating, collecting, and/or recovering a biofuel which is generated by the microorganism (as further detailed below).

The present invention envisages that when the medium comprises formate (and optionally acetate), the doubling time of the microorganism (e.g. bacteria) may be between 1-20 hours, optionally between 3-12 hours for example 4, 5, 6, 7, 8, 9, 10 or 11 hours.

According to one embodiment, the microorganism is one that produces an industrially important product—e.g., a biofuel. Alternatively, or additionally, the microorganism expresses enzymes such that it is capable of producing an industrially important product—e.g., a biofuel. It will be appreciated that the precise choice of enzymes are selected according to the particular microorganism being used. Alternatively, or additionally, the microorganism expresses an industrially important product—e.g., a recombinant protein. Additional industrial important products include antibiotics or other pharmaceutical, solvents, pigments, food additives, monomers for the plastic industry and industrially valuable polymers.

Biofuels include for example, an alcohol (e.g., methanol, ethanol, propanol, isobutanol, and n-butanol etc.), a hydrocarbon (e.g., an alkane such as methane, ethane, propane, butane, an alkene such as ethylene, propylene, isoprenes, an alkyne such as acetylene etc.) hydrogen, a biodiesel (long-chain alkyl (methyl, propyl or ethyl) esters), an aldehyde or ketones (e.g. acetone, formaldehyde, 1-propanal, etc.). The biofuel can be a solid, a liquid or a gas.

Industrially useful microorganisms include the production of ethanol by *Saccharomyces* and the production of butanol by *Clostridium*.

Other industrially useful microorganisms include those in the production of plastic monomers and solvents.

The recombinant protein may be any protein—e.g., a human protein used for medicinal purposes. Examples of such proteins include an antibody, insulin, interferon, growth hormone, erythropoietin, growth hormone, follicle stimulating hormone, factor VIII, low density lipoprotein receptor (LDLR) alpha galactosidase A and glucocerebrosidase.

As mentioned, in order to express recombinant proteins in the microorganism, polynucleotide sequences encoding same are inserted into expression vectors as described herein above.

It will be appreciated that other than containing the necessary elements for the transcription and translation of the inserted coding sequence (encoding the industrially useful polypeptide), the expression construct for expression of the industrially useful polypeptide can also include sequences engineered to optimize stability, production, purification, yield or activity of the expressed polypeptide.

Depending on the vector and host system used for production, resultant polypeptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site (e.g. 26, 27).

Recovery of biofuels may be recovered according to methods known in the art. Alcohols such as ethanol, methanol, and/or butanol may be recovered from liquid material by molecular sieves, distillation, and/or other separation techniques. For example, ethanol can be concentrated by fractional distillation to about 90% or about 95% by weight. There are several methods available to further purify ethanol beyond the limits of distillation, and these include drying (e.g., with calcium oxide or rocksalt), the addition of small quantities of benzene or cyclohexane, molecular sieve, membrane, or by pressure reduction.

Product gas, for example, as produced by anaerobic metabolism or photosynthesis, may be processed to separate the methane and/or hydrogen components. Methane, hydrogen, or biogas may be drawn off from the system as pipeline gas.

In accordance with the invention, methane and/or hydrogen may be recovered as a biofuel product. Methane may be recovered and/or purified from biogas by known methods and systems which are commercially available, including membrane systems known for separating gases on the basis of different permeabilities. See, for example, U.S. Pat. No. 6,601,543, which is hereby incorporated by reference. Alternatively, various methods of adsorption may be used for separating methane and hydrogen.

Other ways of collecting biofuel products including centrifugation, temperature fractionalization, chromatographic methods and electrophoretic methods.

In certain embodiments, the biofuel recovery/purification components may be integrated into the microorganism culturing system (e.g. bioreactor), for example, by connecting the respective device or apparatus to the gas or liquid effluents from the bioreactors. The purified biofuels and bioenergy products may be stoked in a separate container(s).

As mentioned herein above, the microorganisms of the present invention may be used to scavenge acetate from an acetate-containing medium.

Thus, according to another aspect of the present invention there is provided a method of scavenging acetate from an acetate-containing medium comprising contacting the acetate-containing medium with a microorganism which expresses an enzyme which converts, in a single step, acetyl-CoA to pyruvate in the presence of formate, with the medium, thereby scavenging the acetate from the acetate-containing medium.

Acetate accumulation can take place in two main circumstances: (1) in many industrial fermentation processes, acetate accumulates as a result of overflow metabolism; (2) in the hydrolysate of lignocellulosic material, acetate is an unavoidable product of hemicellulose depolymerization because arabinoxylans are acetylated.

Accumulation of acetate can hamper the fermentation process, as it inhibits many central metabolic processes. Several strategies have been suggested to reduce the inhibitory effect of acetate on fermentation, including its chemical removal from the medium, engineering acetate tolerant bacteria and reducing acetate level via its metabolic consumption. In line with this last strategy, the present inventors contemplate that pyruvate synthesis via PFL can be used to reduce the concentration of acetate in the medium. To implement this strategy efficiently, a dedicated strain should be engineered, which relies on PFL to generate pyruvate.

The microorganism may be genetically modified to express PFL or may rely on wild-type strains that express high levels of PFL.

For acetate scavenging, the present inventors contemplate down-regulating or deleting at least one, two, three, four, five or more sugar transport and utilizing genes and overexpressing PFL as described herein above.

Examples of sugar transport and sugar utilizing genes include genes of the phosphotransferase system (PTS) genes (ptsG, manZ, crr), glucokinase (glk), and xylose (xylA). Additional genes include malX, fruA, fruB, bglF, or crr, genes that are involved in other PTSs.

According to a particular embodiment, the microorganism does not express or has a down-regulated level of expression of isocitrate lyase and/or malate synthase. Down-regulation of other genes responsible for acetate assimilation in the host is also contemplated.

Methods of down-regulating genes have been described herein above.

To fuel acetate assimilation this way, it will be appreciated that formate should be present in the medium or produced internally. In the case of overflow metabolism, it is possible that formate is produced alongside acetate (i.e. mixed acid fermentation) and therefore both can be re-assimilated together by the dedicated PFL-dependent strain. In other cases, formic acid can be added to the medium as an auxiliary substrate. Alternatively, the present invention contemplates that the microorganism can be engineered such that it is capable of generating formate from electrons, as further described herein above or by any other means including those described in PCT International Application No. PCT/IL2013/050643, the teachings of which are incorporated herein by reference. Another option is that the organism produces formate endogenously to support acetate assimilation.

As mentioned herein above, the microorganisms of the present invention may be used to scavenge formate from a formate-containing medium. Just as in the case of acetate, accumulation of formate in the fermentation medium (e.g., during mixed acid fermentation) can be deleterious for microbial growth.

Thus, according to another aspect of the present invention there is provided a method of scavenging formate from a formate-containing medium comprising contacting a microorganism which expresses an enzyme which converts, in a single step, acetyl-CoA to pyruvate in the presence of formate with the medium, thereby scavenging the formate from the formate-containing medium.

The microorganism may be genetically modified to express PFL or may rely on wild-type strains that express high levels of PFL.

The acetyl-CoA may be provided to the microorganism from an external source (i.e. addition of acetate to the medium). Alternatively, the microorganisms may be genetically modified as described herein above such that they are capable of generating an internal source of acetyl-CoA.

According to a particular embodiment, the microorganisms of this aspect of the present invention are modified such that the activity of phosphoglyceromutase enzymes, as well as phosphogluconate dehydratase is downregulated. In this way, EMP and ED glycolysis could no longer convert sugars into most of the cellular building blocks.

The present inventors further contemplate overexpressing phosphoketolase in these strains so as to restore the ability of the cell to grow on sugars, as a constant supply of acetyl-CoA becomes available.

The activity of isocitrate lyase may also be down-regulated, thus shutting down the endogenous acetate assimilation pathway. By doing so, the only way for the cell to grow is by assimilating formate through the reverse reaction of PFL. Such a strain can be cultivated alongside the primary fermenting strain, keeping formate concentration within the medium to a minimum.

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Bacteria Expressing PFL and PFL Activating Enzyme to Enable Pyruvate Synthesis from Exogenously Supplied Acetate and Formate The present inventors constructed an *E. coli* strain in which the aceA gene, encoding for isocitrate lyase, was deleted. This strain cannot be cultivated on acetate as it cannot run the isocitrate lyase-dependent glyoxylate shunt (FIG. 1A). The pflA and pflB genes, encoding for PFL-activating enzyme and PFL, respectively, were cloned to the pNiv plasmid, under the regulation of $RBS_C$ ribosome binding sites [39]. The ΔaceA stain was transformed with this plasmid and the bacterium was cultivated at 37° C. under anaerobic conditions on a minimal medium supplemented with 0.2% sodium formate, 0.2% sodium acetate and 25 mM of nitrate as an electron acceptor. As illustrated in FIG. 1B, growth was obtained with a doubling time of 18 hours. The same growth characteristics were obtained also at higher acetate concentration. However, formate concentration could not be increased due to its toxicity. As a control, the present inventors tried to cultivate a ΔaceA stain that harbors a plasmid that contains mcherry instead of the PFL genes, under the same conditions. No growth was observed (FIG. 1B). Also, trying to cultivate the ΔaceA stain, transformed with the PFL plasmid, on a medium without formate, resulted in no growth. These findings demonstrate that the PFL enzyme and its reverse reaction, producing pyruvate, are required to establish growth on acetate in a ΔaceA stain. Notably, in this PFL-dependent strain, >80% of the biomass is derived from PFL-produced pyruvate.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Bar-Even A, Flamholz A, Noor E, Milo R (2012) Rethinking glycolysis: on the biochemical logic of metabolic pathways. Nat Chem Biol 8: 509-517.
2. Romano A H, Conway T (1996) Evolution of carbohydrate metabolic pathways. Res Microbiol 147: 448-455.
3. Verhees C H, Kengen S W, Tuininga J E, Schut G J, Adams M W, et al. (2003) The unique features of glycolytic pathways in Archaea. Biochem J 375: 231-246.
4. Flamholz A, Noor E, Bar-Even A, Liebermeister W, Milo R (2013) Glycolytic strategy as a tradeoff between energy yield and protein cost. Proc Natl Acad Sci USA.
5. Garrigues C, Loubiere P, Lindley N D, Cocaign-Bousquet M (1997) Control of the shift from homolactic acid to mixed-acid fermentation in *Lactococcus lactis*: predominant role of the NADH/NAD+ ratio. J Bacteriol 179: 5282-5287.
6. Melchiorsen C R, Jokumsen K V, Villadsen J, Israelsen H, Arnau J (2002) The level of pyruvate-formate lyase controls the shift from homolactic to mixed-acid product formation in *Lactococcus lactis*. Appl Microbiol Biotechnol 58: 338-344.
7. Derzelle S, Bolotin A, Mistou M Y, Rul F (2005) Proteome analysis of *Streptococcus thermophilus* grown in milk reveals pyruvate formate-lyase as the major upregulated protein. Appl Environ Microbiol 71: 8597-8605.
8. Werner S, Diekert G, Schuster S (2010) Revisiting the thermodynamic theory of optimal ATP stoichiometries by analysis of various ATP-producing metabolic pathways. J Mol Evol 71: 346-355.
9. Wang Q, Ou M S, Kim Y, Ingram L O, Shanmugam K T (2010) Metabolic flux control at the pyruvate node in an anaerobic *Escherichia coli* strain with an active pyruvate dehydrogenase. Appl Environ Microbiol 76: 2107-2114.
10. Lehtio L, Goldman A (2004) The pyruvate formate lyase family: sequences, structures and activation. Protein Eng Des Sel 17: 545-552.
11. Weidner G, Sawers G (1996) Molecular characterization of the genes encoding pyruvate formate-lyase and its activating enzyme of *Clostridium pasteurianum*. J Bacteriol 178: 2440-2444.

12. Asanuma N, Hino T (2002) Molecular characterization and expression of pyruvate formate-lyase-activating enzyme in a ruminal bacterium, *Streptococcus bovis*. Appl Environ Microbiol 68: 3352-3357.
13. Takahashi-Abbe S, Abe K, Takahashi N (2003) Biochemical and functional properties of a pyruvate formate-lyase (PFL)-activating system in *Streptococcus* mutans. Oral Microbiol Immunol 18: 293-297.
14. Sparling R, Islam R, Cicek N, Carere C, Chow H, et al. (2006) Formate synthesis by *Clostridium thermocellum* during anaerobic fermentation. Can J Microbiol 52: 681-688.
15. Pinchuk G E, Geydebrekht O V, Hill E A, Reed J L, Konopka A E, et al. (2011) Pyruvate and lactate metabolism by *Shewanella oneidensis* MR-1 under fermentation, oxygen limitation, and fumarate respiration conditions. Appl Environ Microbiol 77: 8234-8240.
16. Atteia A, van Lis R, Gelius-Dietrich G, Adrait A, Garin J, et al. (2006) Pyruvate formate-lyase and a novel route of eukaryotic ATP synthesis in *Chlamydomonas mitochondria*. J Biol Chem 281: 9909-9918.
17. Hemschemeier A, Jacobs J, Happe T (2008) Biochemical and physiological characterization of the pyruvate formate-lyase PflI of *Chlamydomonas reinhardtii*, a typically bacterial enzyme in a eukaryotic alga. Eukaryot Cell 7: 518-526.
18. Stairs C W, Roger A J, Hampl V (2011) Eukaryotic pyruvate formate lyase and its activating enzyme were acquired laterally from a Firmicute. Mol Biol Evol 28: 2087-2099.
19. Lehtio L, Leppanen V M, Kozarich J W, Goldman A (2002) Structure of *Escherichia coli* pyruvate formate-lyase with pyruvate. Acta Crystallogr D Biol Crystallogr 58: 2209-2212.
20. Hasona A, Kim Y, Healy F G, Ingram L O, Shanmugam K T (2004) Pyruvate formate lyase and acetate kinase are essential for anaerobic growth of *Escherichia coli* on xylose. J Bacteriol 186: 7593-7600.
21. Levanon S S, San K Y, Bennett G N (2005) Effect of oxygen on the *Escherichia coli* ArcA and FNR regulation systems and metabolic responses. Biotechnol Bioeng 89: 556-564.
22. Yang D F, Wei Y T, Huang R B (2007) Computer-aided design of the stability of pyruvate formate-lyase from *Escherichia coli* by site-directed mutagenesis. Biosci Biotechnol Biochem 71: 746-753.
23. Conradt H, Hohmann-Berger M, Hohmann H P, Blaschkowski H P, Knappe J (1984) Pyruvate formate-lyase (inactive form) and pyruvate formate-lyase activating enzyme of *Escherichia coli*: isolation and structural properties. Arch Biochem Biophys 228: 133-142.
24. Becker A, Fritz-Wolf K, Kabsch W, Knappe J, Schultz S, et al. (1999) Structure and mechanism of the glycyl radical enzyme pyruvate formate-lyase. Nat Struct Biol 6: 969-975.
25. Plaga W, Vielhaber G, Wallach J, Knappe J (2000) Modification of Cys-418 of pyruvate formate-lyase by methacrylic acid, based on its radical mechanism. FEBS Lett 466: 45-48.
26. Becker A, Kabsch W (2002) X-ray structure of pyruvate formate-lyase in complex with pyruvate and CoA. How the enzyme uses the Cys-418 thiyl radical for pyruvate cleavage. J Biol Chem 277: 40036-40042.
27. Buis J M, Broderick J B (2005) Pyruvate formate-lyase activating enzyme: elucidation of a novel mechanism for glycyl radical formation. Arch Biochem Biophys 433: 288-296.
28. Vey J L, Yang J, Li M, Broderick W E, Broderick J B, et al. (2008) Structural basis for glycyl radical formation by pyruvate formate-lyase activating enzyme. Proc Natl Acad Sci USA 105: 16137-16141.
29. Sawers G, Watson G (1998) A glycyl radical solution: oxygen-dependent interconversion of pyruvate formate-lyase. Mol Microbiol 29: 945-954.
30. Zhang W, Wong K K, Magliozzo R S, Kozarich J W (2001) Inactivation of pyruvate formate-lyase by dioxygen: defining the mechanistic interplay of glycine 734 and cysteine 419 by rapid freeze-quench EPR. Biochemistry 40: 4123-4130.
31. Alexeeva S, de Kort B, Sawers G, Hellingwerf K J, de Mattos M J (2000) Effects of limited aeration and of the ArcAB system on intermediary pyruvate catabolism in *Escherichia coli*. J Bacteriol 182: 4934-4940.
32. Zhu J, Shalel-Levanon S, Bennett G, San K Y (2007) The YfiD protein contributes to the pyruvate formate-lyase flux in an *Escherichia coli* arcA mutant strain. Biotechnol Bioeng 97: 138-143.
33. Wagner A F, Schultz S, Bomke J, Pils T, Lehmann W D, et al. (2001) YfiD of *Escherichia coli* and Y06I of bacteriophage T4 as autonomous glycyl radical cofactors reconstituting the catalytic center of oxygen-fragmented pyruvate formate-lyase. Biochem Biophys Res Commun 285: 456-462.
34. Hesslinger C, Fairhurst S A, Sawers G (1998) Novel keto acid formate-lyase and propionate kinase enzymes are components of an anaerobic pathway in *Escherichia coli* that degrades L-threonine to propionate. Mol Microbiol 27: 477-492.
35. Sawers G, Hesslinger C, Muller N, Kaiser M (1998) The glycyl radical enzyme TdcE can replace pyruvate formate-lyase in glucose fermentation. J Bacteriol 180: 3509-3516.
36. Zhu J, Shimizu K (2004) The effect of pfl gene knockout on the metabolism for optically pure D-lactate production by *Escherichia coli*. Appl Microbiol Biotechnol 64: 367-375.
37. Himo F, Eriksson L A (1998) Catalytic Mechanism of Pyruvate Formate-Lyase (PFL). A Theoretical Study. J Am Chem Soc 120: 11449-11455.
38. Cortay J C, Negre D, Galinier A, Duclos B, Perriere G, et al. (1991) Regulation of the acetate operon in *Escherichia coli*: purification and functional characterization of the IclR repressor. EMBO J 10: 675-679.
39. Zelcbuch L, Antonovsky N, Bar-Even A, Levin-Karp A, Barenholz U, et al. (2013) Spanning high-dimensional expression space using ribosome-binding site combinatorics. Nucleic Acids Res.
40. Rabaey K, Rozendal R A (2010) Microbial electrosynthesis—revisiting the electrical route for microbial production. Nat Rev Microbiol 8: 706-716.
41. Rabaey K, Girguis P, Nielsen L K (2011) Metabolic and practical considerations on microbial electrosynthesis. Curr Opin Biotechnol 22: 371-377.
42. Bar-Even A, Noor E, Flamholz A, Milo R (2013) Design and analysis of metabolic pathways supporting formatotrophic growth for electricity-dependent cultivation of microbes. Biochim Biophys Acta 1827: 1039-1047.
43. Bar-Even A, Noor E, Lewis N E, Milo R (2010) Design and analysis of synthetic carbon fixation pathways. Proc Natl Acad Sci USA 107: 8889-8894.
44. Bar-Even A, Noor E, Milo R (2012) A survey of carbon fixation pathways through a quantitative lens. J Exp Bot 63: 2325-2342.

45. Mainguet S E, Gronenberg L S, Wong S S, Liao J C (2013) A reverse glyoxylate shunt to build a non-native route from C4 to C2 in *Escherichia coli*. Metab Eng 19: 116-127.
46. Sonderegger M, Schumperli M, Sauer U (2004) Metabolic engineering of a phosphoketolase pathway for pentose catabolism in *Saccharomyces cerevisiae*. Appl Environ Microbiol 70: 2892-2897.
47. Bogorad I W, Lin T S, Liao J C (2013) Synthetic non-oxidative glycolysis enables complete carbon conservation. Nature.
48. Bar-Even A, Noor E, Flamholz A, Milo R (2012) Design and analysis of metabolic pathways supporting formatotrophic growth for electricity-dependent cultivation of microbes. Biochim Biophys Acta.
49. Hartmann T, Leimkuhler S (2013) The oxygen-tolerant and NAD-dependent formate dehydrogenase from *Rhodobacter capsulatus* is able to catalyze the reduction of CO to formate. FEBS J.
50. Chistoserdova L, Chen S W, Lapidus A, Lidstrom M E (2003) Methylotrophy in *Methylobacterium extorquens* AM1 from a genomic point of view. J Bacteriol 185: 2980-2987.
51. Lidstrom M E (2006) Aerobic Methylotrophic Prokaryotes. In: Dworkin M, Falkow S, Rosenberg E, Schleifer K H, Stackebrandt E, editors. The Prokaryotes. New York: Springer. pp. 618-634.
52. Schrader J, Schilling M, Holtmann D, Sell D, Filho M V, et al. (2009) Methanol-based industrial biotechnology: current status and future perspectives of methylotrophic bacteria. Trends Biotechnol 27: 107-115.
53. Beeckmans S (2001) Glyoxylate Cycle. Encyclopedia of Life Science: John Wiley & Sons, Ltd.
54. Erb T J, Berg I A, Brecht V, Muller M, Fuchs G, et al. (2007) Synthesis of C5-dicarboxylic acids from C2-units involving crotonyl-CoA carboxylase/reductase: the ethylmalonyl-CoA pathway. Proc Natl Acad Sci USA 104: 10631-10636.
55. Peyraud R, Kiefer P, Christen P, Massou S, Portals J C, et al. (2009) Demonstration of the ethylmalonyl-CoA pathway by using 13C metabolomics. Proc Natl Acad Sci USA 106: 4846-4851.
56. Anthony C (2011) How half a century of research was required to understand bacterial growth on C1 and C2 compounds; the story of the serine cycle and the ethylmalonyl-CoA pathway. Sci Prog 94: 109-137.
57. Khomyakova M, Bukmez O, Thomas L K, Erb T J, Berg I A (2011) A methylaspartate cycle in haloarchaea. Science 331: 334-337.
58. Xu B, Jahic M, Blomsten G, Enfors S O (1999) Glucose overflow metabolism and mixed-acid fermentation in aerobic large-scale fed-batch processes with *Escherichia coli*. Appl Microbiol Biotechnol 51: 564-571.
59. Enfors S O, Jahic M, Rozkov A, Xu B, Hecker M, et al. (2001) Physiological responses to mixing in large scale bioreactors. J Biotechnol 85: 175-185.
60. Lakshmanaswamy A, Rajaraman E, Eiteman M A, Altman E (2011) Microbial removal of acetate selectively from sugar mixtures. J Ind Microbiol Biotechnol 38: 1477-1484.
61. Kabisch J, Pratzka I, Meyer H, Albrecht D, Lalk M, et al. (2013) Metabolic engineering of *Bacillus subtilis* for growth on overflow metabolites. Microb Cell Fact 12: 72.
62. Horvath I S, Sjode A, Nilvebrant N O, Zagorodni A, Jonsson L J (2004) Selection of anion exchangers for detoxification of dilute-acid hydrolysates from spruce. Appl Biochem Biotechnol 113-116: 525-538.
63. Fernandez-Sandoval M T, Huerta-Beristain G, Trujillo-Martinez B, Bustos P, Gonzalez V, et al. (2012) Laboratory metabolic evolution improves acetate tolerance and growth on acetate of ethanologenic *Escherichia coli* under non-aerated conditions in glucose-mineral medium. Appl Microbiol Biotechnol 96: 1291-1300.
64. Babel W (2009) The Auxiliary Substrate Concept: From simple considerations to heuristically valuable knowledge. Eng Life Sci 9: 285-290.
65. Berrios-Rivera S J, Bennett G N, San K Y (2002) Metabolic engineering of *Escherichia coli*: increase of NADH availability by overexpressing an NAD(+)-dependent formate dehydrogenase. Metab Eng 4: 217-229.

What is claimed is:

1. An isolated microorganism that is a bacterium or yeast, that is genetically modified to express a pyruvate formate lyase (PFL) or to express a 2-ketobutyrate formate lyase, wherein the microorganism further expresses a polypeptide which activates said PFL, wherein the microorganism does not express isocytrate lyase (aceA) and or malate synthase, wherein the microorganism is capable of converting acetyl CoA to pyruvate, wherein the source of said acetyl coA is:
   (i) internal metabolism; or
   (ii) externally supplied acetate in a medium,
   wherein said medium comprises an amount of formate and/or acetate which favors the net flux of the reaction to be in the direction of pyruvate synthesis.

2. The isolated microorganism of claim 1, wherein said pyruvate formate lyase is encoded by a gene selected from the group consisting of pflB, pflD and ybiW.

3. The microorganism of claim 1, that is capable of generating an internal source of acetyl-CoA.

4. The microorganism of claim 1, that is formatotrophic.

5. The microorganism of claim 3, that expresses at least one enzyme selected from the group consisting of pyruvate carboxylase, malate dehydrogenase, malate-CoA ligase and malyl-CoA lyase.

6. The microorganism of claim 1, that is a bacterium.

7. The microorganism of claim 6, wherein said bacterium comprises *Escherichia*.

8. The microorganism of claim 1, that is incapable of transporting and utilizing sugar.

9. The microorganism of claim 8, not expressing at least one of the enzymes selected from the group consisting of phosphoglyceromutase, isocitrate lyase and phosphogluconate dehydratase.

10. The microorganism of claim 1, that is a yeast.

11. The microorganism of claim 1, capable of producing a biofuel.

12. A system for culturing the microorganism of claim 4 and an electrode for providing electrons to generate formate from $CO_2$.

13. A cell culture comprising the isolated microorganism of claim 1 and a medium suitable for propagation of the microorganism.

14. A cell culture, comprising an isolated microorganism being genetically modified to express an enzyme of a reaction which converts acetyl-CoA of the microorganism to pyruvate in the presence of formate in a single step, and a medium comprising an amount of acetate and/or formate which favors the net flux of the reaction to be in the direction of pyruvate synthesis.

15. The cell culture of claim 13, wherein the medium comprises an amount of acetate and/or formate which favors the net flux of the reaction to be in the direction of pyruvate synthesis.

16. A method of generating a biofuel comprising culturing the microorganism of claim 11 under conditions that allow for biofuel formation, thereby generating the biofuel.

17. A method of scavenging acetate from an acetate-containing medium comprising contacting the microorganism of claim 1, with said medium, thereby scavenging the acetate from the acetate-containing medium.

18. A method of scavenging formate from a formate-containing medium comprising contacting the microorganism of claim 1 with said medium, thereby scavenging the formate from the formate-containing medium.

* * * * *